(12) United States Patent
Niedzwiecki et al.

(10) Patent No.: US 11,666,643 B1
(45) Date of Patent: *Jun. 6, 2023

(54) MICRONUTRIENT COMBINATION TO REDUCE BLOOD PRESSURE

(71) Applicant: Matthias W Rath, Henderson, NV (US)

(72) Inventors: Aleksandra Niedzwiecki, Henderson, NV (US); Matthias W Rath, Henderson, NV (US); Vadim Ivanov, Castro Valley, CA (US); Waldemar Sumera, SanJose, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/070,224

(22) Filed: Nov. 28, 2022

Related U.S. Application Data

(62) Division of application No. 17/579,563, filed on Jan. 19, 2022, now Pat. No. 11,571,468.

(51) Int. Cl.
| | |
|---|---|
| A61K 38/55 | (2006.01) |
| A61P 9/12 | (2006.01) |
| A61K 31/375 | (2006.01) |
| A61K 31/4415 | (2006.01) |
| A61K 31/51 | (2006.01) |
| A61K 31/525 | (2006.01) |
| A61K 31/593 | (2006.01) |
| A61K 31/714 | (2006.01) |
| A61K 36/23 | (2006.01) |
| A61K 36/61 | (2006.01) |
| A61K 36/87 | (2006.01) |

(52) U.S. Cl.
CPC .......... *A61K 38/556* (2013.01); *A61K 31/375* (2013.01); *A61K 31/4415* (2013.01); *A61K 31/51* (2013.01); *A61K 31/525* (2013.01); *A61K 31/593* (2013.01); *A61K 31/714* (2013.01); *A61K 36/23* (2013.01); *A61K 36/61* (2013.01); *A61K 36/87* (2013.01); *A61P 9/12* (2018.01)

(58) Field of Classification Search
None
See application file for complete search history.

(56) References Cited

PUBLICATIONS

Dietary supplement ingredient database (<https://dsid.od.nih.gov/Conversions.php> accessed Dec. 29, 2022.*
Dr. Rath Healthy Blood Pressure (https://shop.drrath.com/products/dr-rath-healthy-blood-pressure-synergy-formula?currency=USD&variant=355750519&utm_medium=cpc&utm_source=google&utm_campaign=Google%20Shopping&gclid=CjwKCAjw9LSSBhBsEiwAKtf0nzoB1WNKia1eQGDyVmJgCj2TXq9xLAVMaqFExvg6rXwNbsDXxRwL5RoCJ58QAvD_BwE.*
Lisinopril Solution—WebMD (available online Jul. 12, 2011).*

* cited by examiner

*Primary Examiner* — Julie Ha
*Assistant Examiner* — Tara L Martinez
(74) *Attorney, Agent, or Firm* — Geeta Kadambi; Riddhi IP LLC

(57) ABSTRACT

A micronutrient composition comprises of vitamin C, vitamin D3, vitamin B1, vitamin B2, vitamin B3, vitamin B6, vitamin B9 and vitamin B12, magnesium, clove extract, grape extract, celery extract and L-arginine. This micronutrient composition supports critical cellular mechanisms involved in the relaxation of vascular smooth muscle cells important in maintaining healthy blood pressure.

7 Claims, 6 Drawing Sheets

| Micronutrient composition, mcg/ml | Control | 1 | 3 | 10 | 30 | 100 | 300 | No Cell Control |
|---|---|---|---|---|---|---|---|---|
| Gel Contraction, % of Control | 100 | 98 | 98 | 87 | 73 | 39 | 25 | 0 |
| Representative Gel Image | 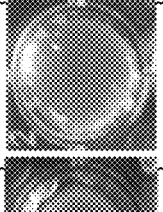 | 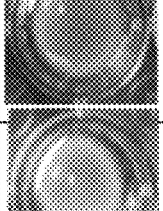 | | 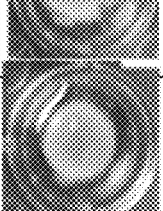 | | 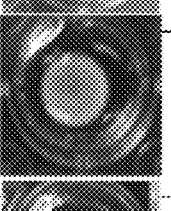 | |  |
Figures 3A, 3B, 3C, 3D, 3E, 3F, 3G, 3H

MICRONUTRIENT COMBINATION TO REDUCE BLOOD PRESSURE

CROSS REFERENCE TO RELATED APPLICATIONS

This application is a divisional application to U.S. application Ser. No. 17/579,563 filed on Jan. 19, 2022. The disclosure is hereby incorporated by this reference in their entirety for all of their teachings.

FIELD OF STUDY

This application discloses micronutrient combination to reduce high blood pressure using the composition in mammal.

BACKGROUND

According to Mayo clinic web site most people with high blood pressure have no signs or symptoms, even if blood pressure readings reach dangerously high levels. Hypertension may cause headaches, shortness of breath or nosebleeds, but these signs and symptoms aren't specific and usually don't occur until high blood pressure has reached a severe or life-threatening stage. Established risk factors are, among others, chronic stress, unhealthy nutrition and lack of exercise. Common pharmaceutical treatments, including angiotensin-converting enzyme inhibitors, calcium-channel blockers, diuretics are merely mitigating symptoms and generally require life-long treatment. Thus, there exists the need for an additional approach addressing the underlying metabolic dysfunction in smooth muscle cells and other vascular cells involved in vascular constriction and relaxation and, thereby, the regulation of blood pressure. Micronutrients are cofactors in a multitude of cellular metabolic processes and prime candidates in correcting dysfunction of vascular cells and hypertensive conditions.

SUMMARY

The instant micronutrient composition prevents, treats and delays high blood pressure and helps reduce secondary effects of high blood pressure. In one embodiment, a blood pressure reducing micronutrient composition is disclosed. In one embodiment, the instant blood pressure reducing micronutrient composition relaxes the blood vessels to delay high blood pressure and helps reduce secondary effects of high blood pressure. In one embodiment, a blood pressure reducing micronutrient composition as disclosed relaxes the blood vessels and enables to reduce headache and other conditions related to vascular constriction. In another embodiment, the instant micronutrient composition relaxes smooth muscle cells in other organ systems and helps to prevent and correct pathological conditions associated with smooth muscle constriction, including in the respiratory tract (e.g. asthma), the uterus (e.g. premenstrual syndrome cramps) etc. In one embodiment blood pressure reducing micronutrient composition comprises of a combination of vitamin C, vitamin D3, vitamin B1, vitamin B2, vitamin B3, vitamin B6, vitamin B9 (folate) and vitamin B12, magnesium, calcium, clove extract, grape extract, celery extract and L-arginine are disclosed. In another embodiment, the mixture either individually or in combination is used for treating high blood pressure in mammals including human. In another embodiment blood pressure reducing micronutrient composition comprising or consisting of a combination of vitamin C, vitamin D3, vitamin B1, vitamin B2, vitamin B3, vitamin B6, vitamin B9 (folate) and vitamin B12, calcium and magnesium, clove extract, grape extract, celery extract and L-arginine are disclosed.

The micronutrient composition, comprising of vitamin C, vitamin D3, vitamin B1, vitamin B2, vitamin B3, vitamin B6, vitamin B9 and vitamin B12 and calcium, magnesium, clove extract, grape extract, celery extract and L-arginine, wherein the vitamin C in form of an ascorbate, wherein the ascorbate is selected from water-soluble or lipid-soluble ascorbates, or mixtures thereof, preferably from calcium ascorbate, magnesium ascorbate, sodium ascorbate, ascorbyl phosphate, ascorbyl palmitate or mixtures thereof.

The micronutrient composition contains the nutrients as single dose or per daily dose in the following ranges: Vitamin C (Calcium ascorbate or magnesium ascorbate) in the range of 0.01 mg-5000 mg, Vitamin B1 in the range of 0.1 mg-50 mg, Vitamin B2 in the range of 0.1 mg-50 mg, Vitamin B3 in the range of 1 mg-3000 mg, Vitamin B6 in the range of 0.1 mg-50 mg, vitamin B9 (folate) in the range of 10 mcg-10000 mcg, Vitamin B12 in the range of 10 µg-300 µg Vitamin D in the range of 10 mg 400 mg, magnesium in the range of 1 mg-5,000 mg, celery extract in the range of 10 mg-2000 mg, Grape seed extract in the range of 10 mg-1000 mg, Clove extract in the range of 10 mg-10000 mg, green tea extract in the range of 10 mg-1000 mg and L-Arginine in the range of 10 mg-2000 mg.

In one embodiment, a method of treating a mammal with micronutrient composition comprising of a combination of vitamin C, vitamin D3, vitamin B1, vitamin B2, vitamin B3, vitamin B6, vitamin B9 (folate) and vitamin B12, magnesium, clove extract, grape extract, celery extract and L-Arginine is formulated as a tablet, coated tablet, capsule, pill, lozenges, emulsion, pastilles, suppository, paste and injectable solution for a mammalian consumption are disclosed.

The micronutrient composition may be co-prescribed with other high blood pressure lowering pharmaceutical drugs. It may be beneficial to co-prescribe them as that would reduce the pharmaceutical dose and prevent an individual from exposure of long term pharmaceutical drug use.

Finally, the present invention is described further in the detailed description to further illustrate various aspects of the present invention.

BRIEF DESCRPTION OF DRAWINGS

Example embodiments are illustrated by way of example only and not limitation, with reference to the figures of the accompanying drawings, in which like references indicate similar elements and in which:

FIGS. 3A, 3B, 3C, 3D, 3E, 3F, 3G, 3H shows the photographs of dose-dependent effects of reconstituted micronutrient composition on collagen gel contraction by aortic smooth muscle cells.

Figure 1:
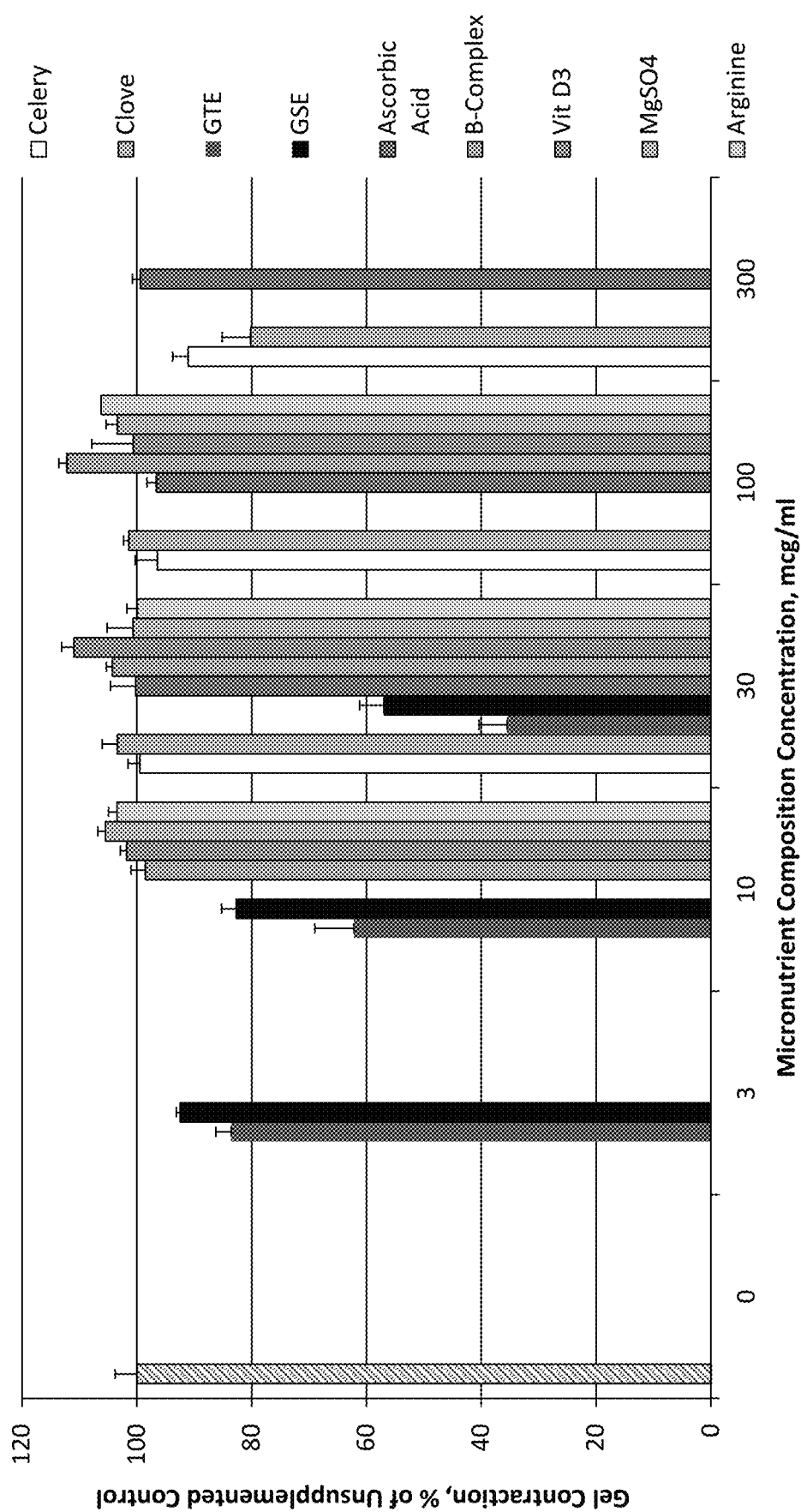
FIG. 1 shows effects of individual components of the micronutrient composition used as a blood pressure formula on collagen gel contraction by aortic smooth muscle cells.

Other features of the present disclosure will be apparent from the accompanying drawings and from the detailed description of embodiments that follows.

DETAILED DESCRIPTION

Many combinations of micronutrients have been used for treating and reducing high blood pressure. However, in the instant invention a combination of micronutrients as a micronutrient composition as shown in table 1 and table 2 below makes a good combination and is highly effective. The said range shown in the table is optimal for 1 dosage. However, the range for concentration may be broader or narrower than described. The combination of micronutrients may be taken as 1 dose or multiple doses. It may be taken multiple times a day with or without prescription medication to lower high blood pressure. Physiological dose range for mammal consumption, such as human, has been calculated as below:

Vitamin C (Calcium ascorbate or magnesium ascorbate) in the range of 0.01 mg-5000 mg, Vitamin B1 in the range of 0.1 mg-50 mg, Vitamin B2 in the range of 0.1 mg-50 mg, Vitamin B3 in the range of 1 mg-3000 mg, Vitamin B6 in the range of 0.1 mg-50 mg, vitamin B9 (folate) in the range of 10 mcg-10000 mcg, Vitamin B12 in the range of 10 µg-300 µg, Vitamin D in the range of 10 mg 400 mg, magnesium in the range of 1 mg-5,000 mg, celery extract in the range of 10 mg-2000 mg, Grape seed extract in the range of 10 mg-1000 mg, Clove extract in the range of 10 mg-10000 mg, green tea extract in the range of 10 mg-1000 mg and L-Arginine in the range of 10 mg-2000 mg. The physiological dose is shown in a range after calculating from invivo studies, that it is suitable for various methods of delivery or consumption. Since different modes of delivery of micronutrient composition depend on many factors such as different absorption, severity, individual differences, absorption, but not limited to these the concentration is different.

Method of treating a mammal, such as human, to lower the blood pressure with or without the prescribed medication is done using the micronutrient formula comprising in a range Vitamin C (Calcium ascorbate or magnesium ascorbate) in the range of 0.01 mg-5000 mg, Vitamin B1 in the range of 0.1 mg-50 mg, Vitamin B2 in the range of 0.1 mg-50 mg, Vitamin B3 in the range of 1 mg-3000 mg, Vitamin B6 in the range of 0.1 mg-50 mg, vitamin B9 (folate) in the range of 10 mcg-10000 mcg, Vitamin B12 in the range of 10 µg-300 µg, Vitamin D in the range of 10 mg 400 mg, magnesium in the range of 1 mg-5,000 mg, celery extract in the range of 10 mg-2000 mg, Grape seed extract in the range of 10 mg-1000 mg, Clove extract in the range of 10 mg-10000 mg, green tea extract in the range of 10 mg-1000 mg and L-Arginine in the range of 10 mg-2000 mg. The prescribed medication can be Lisinopril or any other blood pressure lowering medication.

Celery extract has been shown in animal studies to help prevent stroke, improve blood flow, and act to protect the brain and enhance energy production. GSEs (grape seed extracts) which contain polyphenolic compounds cause an endothelium-dependent relaxation of blood vessels. The active component of clove—Eugenol activates TRPV4 channels in mesentery artery endothelial cells, leading to vasorelaxation, and reduces systemic BP in vivo. Eugenol may be therapeutically useful as an antihypertensive agent and is a viable molecular candidate from which to develop second-generation TRPV4 channel activators that reduce blood pressure.

B complex vitamins have been studied for ages and have been found that there was a significant decrease of systolic blood pressure, homocysteine, and malondialdehyde (MDA) blood levels in animals under B vitamin supplementation. The treatment with B-vitamins also inhibited the neurological signs of an ischemic attack (unbalance, ataxia, and convulsions). The findings reported here suggest that vitamin B therapy was effective for the control of systolic blood pressure and oxidative stress. Hence, it could be thought as one of the alternative therapies to prevent the occurrence of stroke. Plasma vitamin C concentration has been inversely associated with blood pressure in both men and women. Vitamin C has protective effects on blood vessels and increases availability of NO that has relaxing effect on blood vessel walls.

The said combination has never been evaluated. The said combination may be used in solid, liquid, tablet or any form suitable for absorption and digestion. The said combination of micronutrients may be given to a human with other medications.

Methods: Collagen Gel Contraction driven by Human Aortic smooth muscle cells (HASMC) has been used for testing an ability of different concentrations of micronutrient composition to inhibit contractile action of smooth muscle cells. All experiments were done in triplicates and results are expressed as mean values +/− SD. FIG. 1 present the effects of individual compounds applied in the ranges between 3 mcg/ml to 300 mcg/ml on the contractile properties of human aortic smooth muscle cells embedded in collagen gel. Aortic smooth muscle driven changes in gel contraction are expressed as % of un-supplemented control. Observed effective concentration ranges for all tested compounds are between 10 and 100 mcg/ml.

Reconstituted micronutrient composition to be used for gel contraction assay: Individual components were dissolved in ethanol, dimethyl sulfoxide or water as appropriate to prepare corresponding stock solutions. For experimental testing stock solutions were diluted with DMEM cell culture medium to reach indicated concentrations. Reconstituted micronutrient composition was prepared as indicated in Table 1.

TABLE 1

Composition of reconstituted micronutrient composition.

| NN | Individual Components | Content in Micronutrient composition as a daily dose (mg) | Content per 100 mcg of Micronutrient composition, mcg |
|----|----------------------|-----|-----|
| 1 | Ascorbic Acid | 200 | 11.7 |
| 2 | Vitamin D3 | 0.05 | 0.00292 |
| 3 | Vitamin B-Complex Contains: vitamin B1 4% of total weight, vitamin B2 6.3%, vitamin B3 57.5%, vitamin B5 25.7%, vitamin B6 5.3%, vitamin C12- 0.01%, Folic acid 0.8% (vitamin B 9) and Biotin 0.2%) | 30 | 1.8 |
| 4 | Magnesium Sulfate | 213 | 12.4 |
| 5 | Celery Extract | 150 | 8.8 |
| 6 | Green Tea Extract | 200 | 11.7 |
| 7 | Grape Seed Extract | 400 | 23.3 |
| 8 | Clove Extract | 400 | 23.3 |
| 9 | Arginine monohydrochloride | 121 | 7.1 |

TABLE 2

Micronutrient composition tested in ACE activity and NO studies.

| NN | Individual Components | Content in Micronutrient composition daily dose (4 capsules), mg | Content of individual compounds per 100 mcg of Micronutrient composition, mcg |
|---|---|---|---|
| 1 | Ascorbic Acid | 400 | 15 |
| 2 | Vitamin D3 | 0.05 | 0.002 |
| 3 | Vitamin B-Complex (vitamin B1-5 mg, vitamin B2-5 mg, vitamin B3-10 mg, vitamin B6-5 mg, vitamin B9 -Folate) - 0.4 mg, vitamin B12-0.05 mg) | 30 | 1.1 |
| 4 | Magnesium | 400 | 15 |
| 5 | Calcium | 33 mg | 1.24 |
| 6 | Celery Extract | 300 | 11.3 |
| 7 | Green Tea Extract | 450 | 16.9 |
| 8 | Grape Seed Extract | 450 | 16.9 |
| 9 | Clove Extract | 450 | 16.9 |
| 10 | Arginine monohydrochloride | 150 | 5.6 |

Gel Contraction Assay: HASMS were obtained from Lonza Corporation and cultured in DMEM cell culture medium (ATCC) supplemented with 5% fetal bovine serum (ATCC). For experiments cells were suspended in DMEM medium at 500,000 per mL by trypsinization and mixed with equal volume of 2 mg/ml bovine skin collagen (Sigma) solution in DMEM. Resulting cell suspension was distributed at 300 mcl per well of plastic 24 well plate pretreated with 10 mg/ml bovine serum albumin in phosphate buffered saline. Collagen gels, formed in the wells after one hour incubation at 37° C., were supplemented with 500 mcl DMEM containing indicated amounts of tested micronutrient composition. After 24 hours incubation at 37° C. pictures of the wells were taken with digital photo camera and gel surface area was measured in pixels using ImageJ scientific software. Gel contraction was expressed as percentage of unsupplemented control using the following formula:

(No Cell Control Gel Area−Tested Sample Gel Area)/(No Cell Control Gel Area−Not Supplemented Control Gel Area)*100%.

Figure 2:
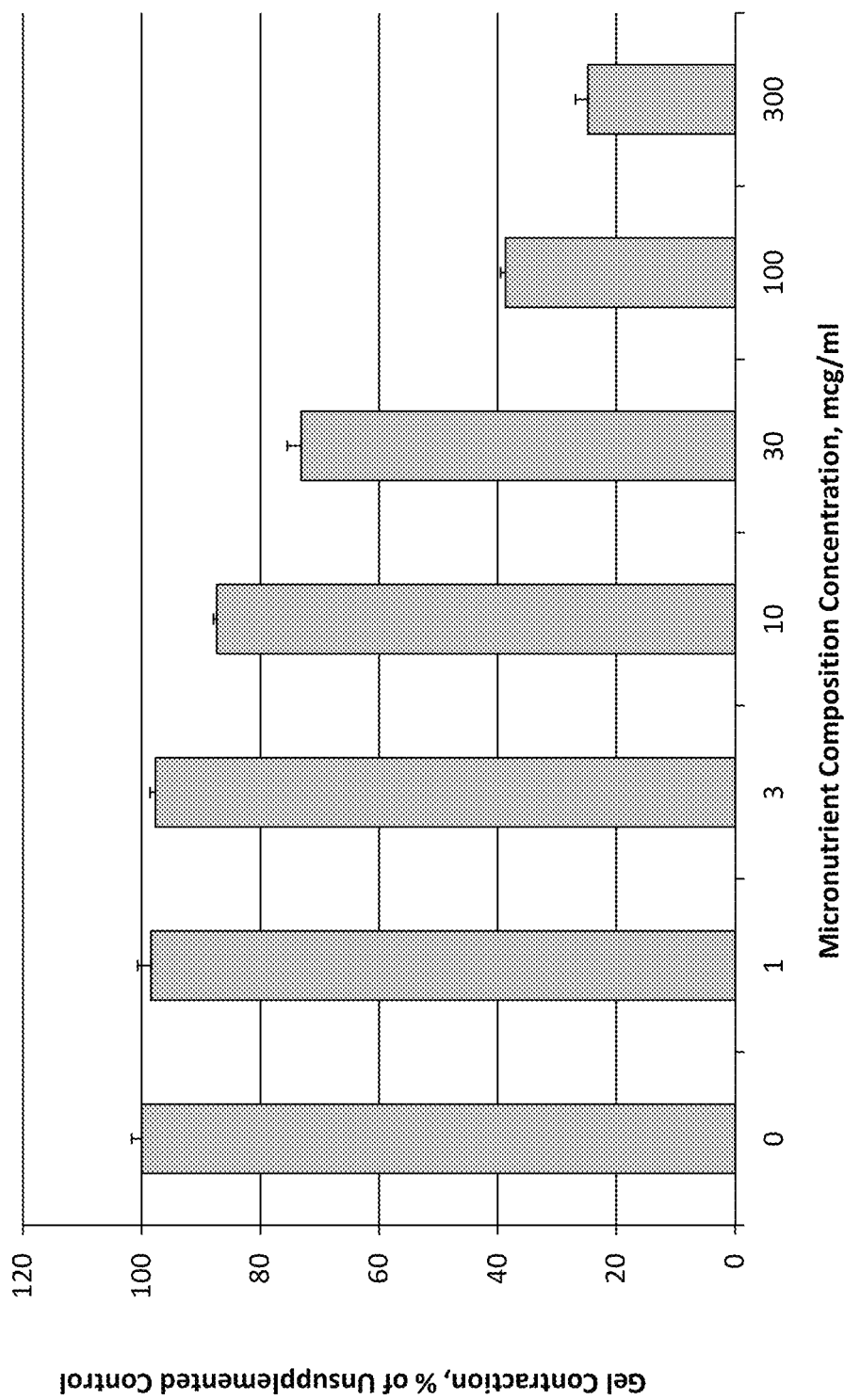
FIG. 2 shows dose-dependent effects of reconstituted micronutrient composition on Collagen Gel Contraction by aortic smooth muscle cells.

FIG. 2 present the concentration dependent effects of the reconstituted micronutrient composition (as specified in Table 3) on the contractile properties of human aortic smooth muscle cells embedded in collagen gel. Aortic smooth muscle cells driven changes in the gel contraction are expressed as % of un-supplemented control. Tested formula concentrations were between 1 mcg/ml to 300 mcg/ml. Observed gel relaxing effect started at 10 mcg/ml (13% relaxation) and was more pronounced in the presence of 100 mcg/ml (at 61%) and 300 mcg/ml (75% relaxation).

TABLE 3

Dose-dependent Effects of Reconstituted Micronutrient composition on Collagen Gel Contraction by Aortic Smooth Muscle Cells

| | BPF, mcg/ml | | | | | | | |
|---|---|---|---|---|---|---|---|---|
| | Control | 1 | 3 | 10 | 30 | 100 | 300 | No Cell Control |
| Gel Contraction, % of Control | 100 | 98 | 98 | 87 | 73 | 39 | 25 | 0 |
| Image correlation | FIG. 3A | FIG. 3B | FIG. 3C | FIG. 3D | FIG. 3E | FIG. 3F | FIG. 3G | FIG. 3H |

FIGS. 3A, 3B, 3C, 3D, 3E, 3F, 3G, 3H shows the images of the aortic smooth muscle gels exposed to different concentrations of the formula with corresponding numerical values of each gel contraction compared to unsupplemented control.

Figure 4:
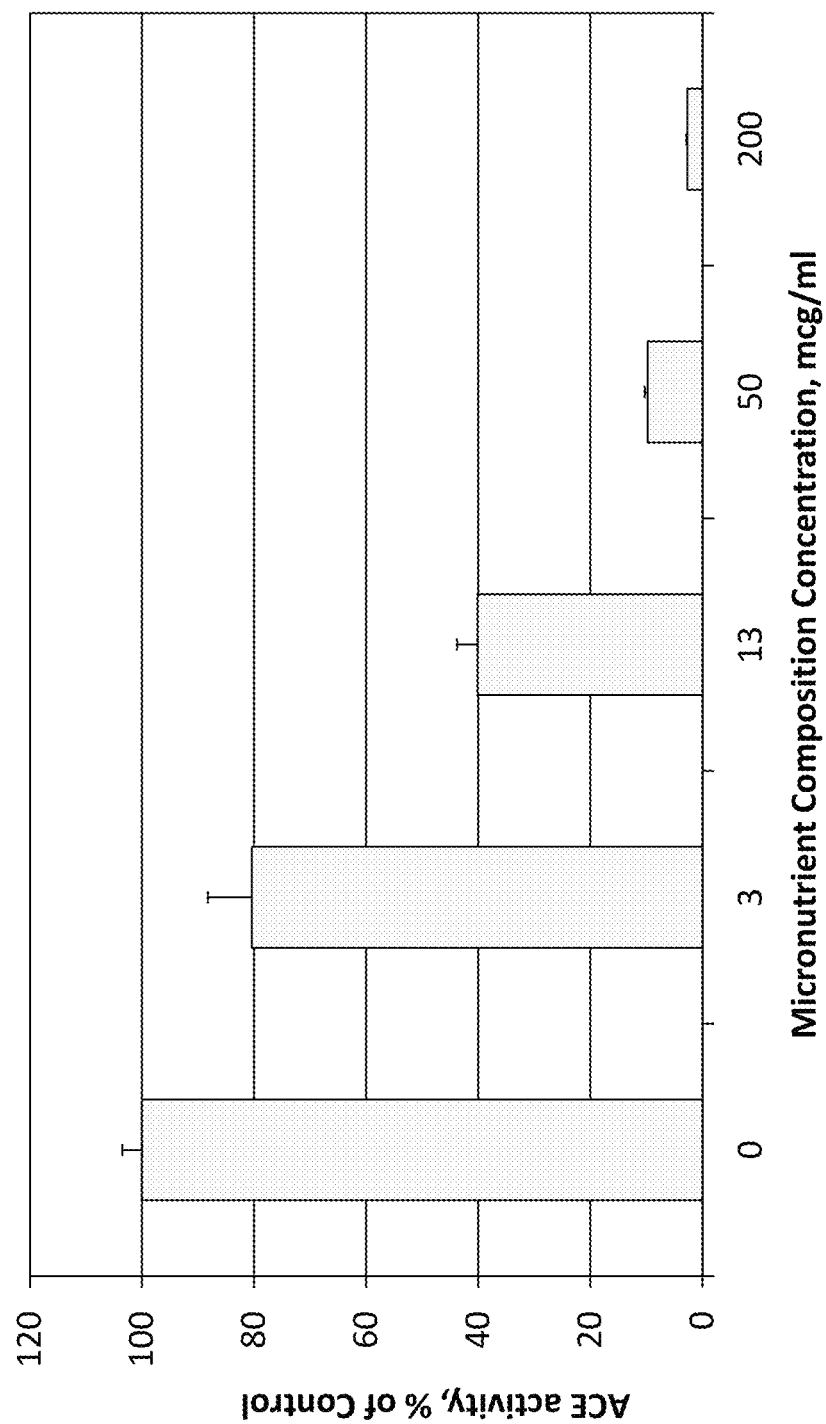
FIG. 4 shows direct effects of micronutrient composition on catalytic activity of recombinant Angiotensin I Converting Enzyme.
Figure 5:
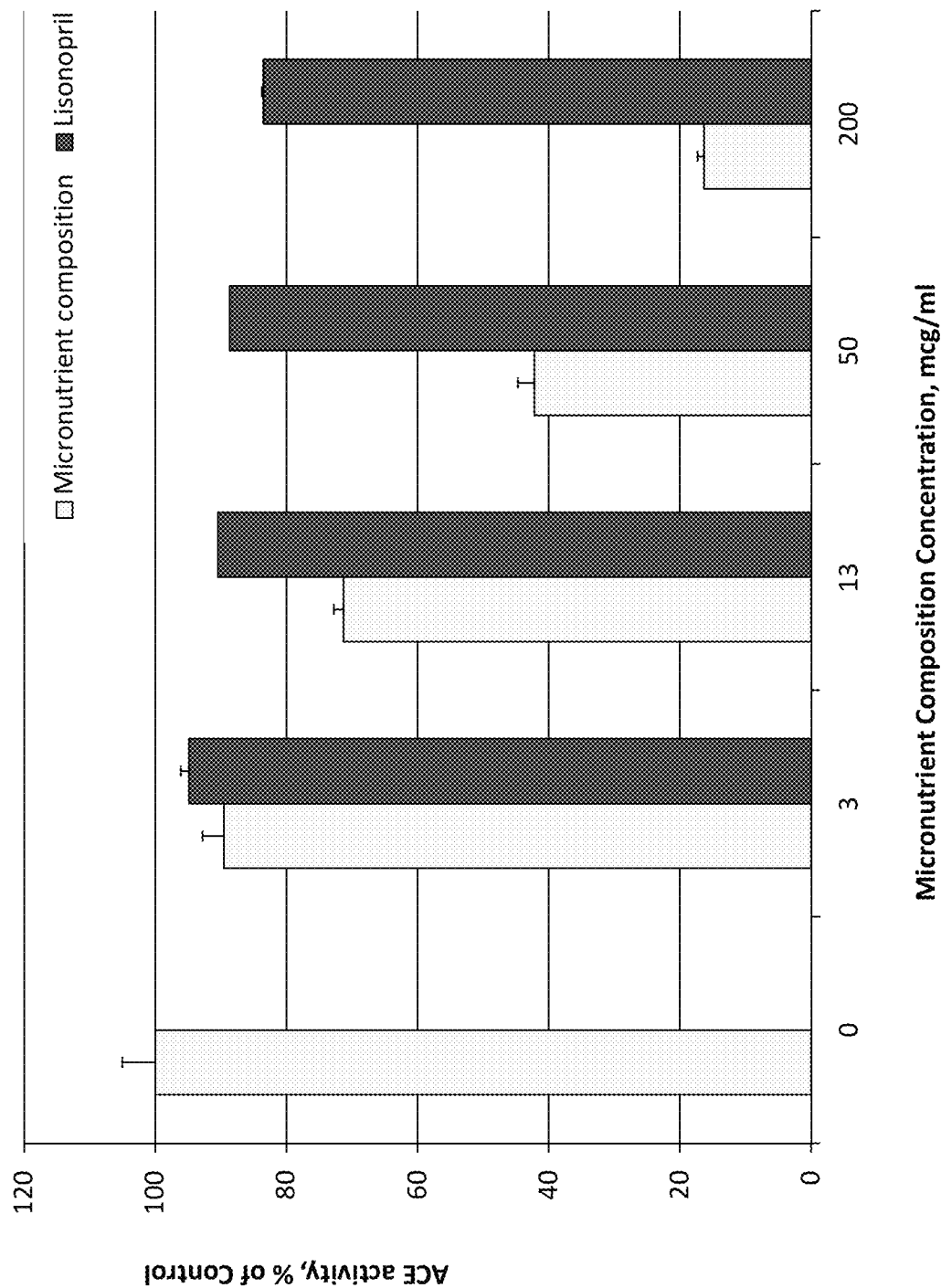
FIG. 5 shows the effects of micronutrient composition and Lisinopril on catalytic activity of Angiotensin I Converting Enzyme Isolated on cultured human aortic endothelial cells.

ACE 1 activity: Effects of New Micronutrient composition on catalytic activity of Angiotensin I Converting Enzyme (ACE) was analyzed using recombinant catalytic ACE domain (Sigma) or ACE isolated from cultured human aortic endothelial cells (AoEC) with ACE Activity Assay Kit (Fluorometric, Sigma, Catalog Number CS0002) in accordance with manufacturer's protocol. For preparation of cell lysate ACE human AoEC (Lonza) were plated in 75 cm2 plastic flask at 6th passage and cultured with EGB-2 endothelial cell culture medium (Lonza) in 5% CO2 at 37 oC until cell forming a confluent layer. Cells were washed twice with 10 ml phosphate buffered solution (PBS) and lysated by scratching and resuspending in 5 ml CelLytic™ M solution (Sigma) after 15 min incubation at room temperature. Results are expressed as percentage of untreated controls presented as averages +/− SD from three replicates. The results on FIG. 4 show concentration dependent inhibitory effect of the micronutrient composition for blood pressure lowering on catalytic activity of Angiotensin1 converting enzyme. Changes in ACE1 activity are expressed in % compared to control. The formula applied at 3 mcg/ml inhibits ACE1 by 20% with the most pronounced inhibitory effect of 90% and 97% obtained at 50 mcg/ml and 200 mcg/ml respectively. FIG. 5 shows the concentration dependent effects of the micronutrient composition for blood pressure lowering and a pharmaceutical drug Lisinopril on catalytic activity of Angiotensin 1 converting enzyme. Lisinopril is a prescription medication belonging to a class of ACE inhibitors and used to treat high blood pressure. Changes in ACE1 activity are expressed in % compared to control. The inhibitory effect of the formula on ACE1 activity was observed between 3 mcg/ml and 200 mcg/ml, with maximum 84% inhibition obtained at 200 mcg/ml. Lisinopril applied at this concentration range showed only slight inhibitory effects with 16% inhibition of ACE1 activity observed at 200 mcg/ml concentration.

Figure 6:
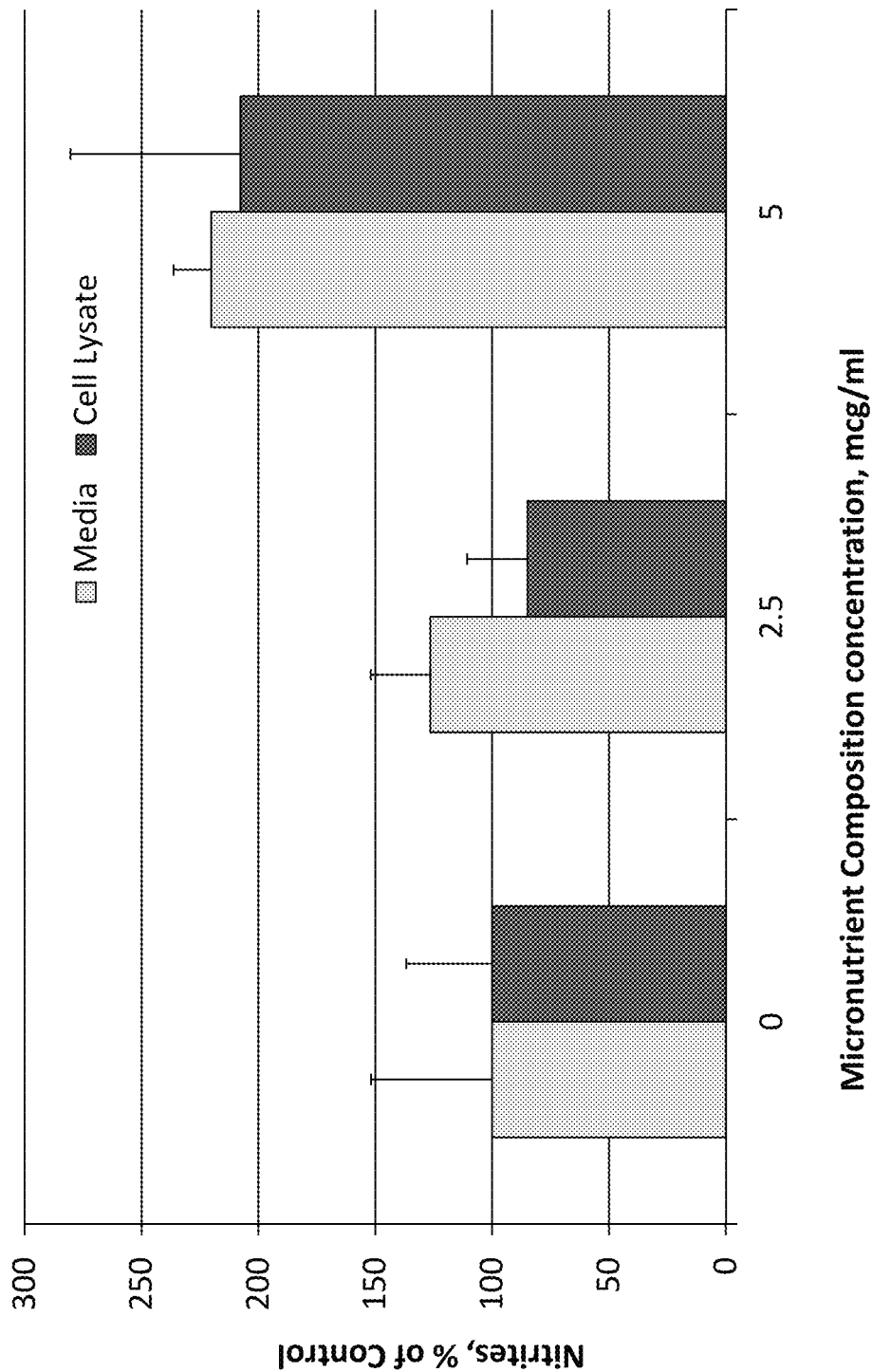
FIG. 6 shows effects of micronutrient composition on nitric oxide (NO) accumulation and secretion in cultured human Aortic Endothelial Cells.

Nitric Oxide production by cultured human aortic endothelial cells: Human AoEC (Lonza) were plated in six well plastic plates at 6th passage and cultured with EGB-2 medium (Lonza) until cell forming a confluent layer. Cells were supplemented with increasing concentrations of Micronutrient composition in EGB-2 medium for three days. Conditioned cell culture medium samples were collected and analyzed immediately for Nitric oxide (NO) content using Nitric Oxide Assay Kit (Fluorometric, Abcam #ab65327) according to manufacturer's protocol. For intracellular NO content cell layers were washed twice with PBS, lysed with Assay Buffer (ABCAM), and then analyzed for NO content as described above. Results are expressed as percentage of untreated controls presented as averages +/− SD from at least two replicates. The results on FIG. 6 show concentration dependent inhibitory effect of the micronutrient composition on NO secretion and accumulation in human aortic endothelial cells. Changes in NO production by the cells is expressed as % of nitrites compared to control. The formula applied at 5 mcg/ml had stimulating effect on NO secretion (120% increase compared to control) and its intracellular production (108% increase).

Instant micronutrient composition supports relaxation of aortic smooth muscle cells, important in maintain healthy blood pressure. It increases production of NO ("relaxing factor") and decreases activity of Angiotensin converting enzyme 1 (ACE1) better than pharmaceutical ACE1 inhibitor—Lisinopril—commonly prescribed high blood pressure medication.

Drug formulations suitable for these administration routes can be produced by adding one or more pharmacologically acceptable carrier to the agent and then treating the micronutrient composition through a routine process known to those skilled in the art. The mode of administration includes, but is not limited to, non-invasive peroral, topical (for example, transdermal), enteral, transmucosal, targeted delivery, sustained-release delivery, delayed release, pulsed release and parenteral methods. Peroral administration may be administered both in liquid and dry state. In one embodiment, micronutrient composition is to be used specifically for micronutrient composition for reducing blood pressure. It may be co-administered—with Lisinopril.

The micronutrient composition may have the components in the range of Vitamin C (Calcium ascorbate or magnesium ascorbate) in the range of 0.01 mg-5000 mg, Vitamin B1 in the range of 0.1 mg-50 mg, Vitamin B2 in the range of 0.1 mg-50 mg , Vitamin B3 in the range of 1 mg-3000 mg, Vitamin B6 in the range of 0.1 mg-50 mg, vitamin B9 (folate) in the range of 10 mcg-10000 mcg, Vitamin B12 in the range of 10 μg-300 μg, Vitamin D in the range of 10 mg 400 mg, magnesium in the range of 1 mg-5,000 mg, celery extract in the range of 10 mg-2000 mg, Grape seed extract in the range of 10 mg-1000 mg, Clove extract in the range of 10 mg-10000 mg, green tea extract in the range of 10 mg-1000 mg and L-Arginine in the range of 10 mg-2000 mg. These are just examples of the range depending on the mode of introduction of the micronutrient composition for treating high blood pressure. The upper range and lower range may be adjusted according to patient requirement and mode of manufacturing to be optimally suited for treating a mammal and lowering the blood pressure, relaxing the artery, reducing headache or relieving respiratory discomforts.

Formulations suitable for oral administration may be in the form of capsules, cachets, pills, tablets, lozenges (using a flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of a subject composition as an active ingredient. Subject compositions may also be administered as a bolus, electuary or paste.

When an oral solid drug product is prepared, micronutrient composition is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, rice powder, L-leucine, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, orange peel, citric acid and tartaric acid.

When a liquid drug product for oral administration is prepared, micronutrient composition is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin.

For the purposes of transdermal (e.g., topical) administration, dilute sterile, aqueous or partially aqueous solutions (usually in about 0.1% to 5% concentration), otherwise similar to the above parenteral solutions, may be prepared with micronutrient composition.

Formulations containing micronutrient composition for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing micronutrient composition can be added to the extended-release system by means of either applying an immediate-release layer on top of the extended release core; using coating or compression processes, or in a multiple-unit system such as a capsule containing extended- and immediate-release beads.

When used with respect to a micronutrient composition, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the micronutrient composition is released over a period of time in a controlled manner from a formulation. Types of sustained release formulations include liposomes, drug-loaded biodegradable microspheres and micronutrient composition polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a micronutrient composition with a selected coating material. The micronutrient composition may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using the instant micronutrient composition.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

Certain micronutrient composition disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, micronutrient composition is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the micronutrient compositions described herein are formulated in a manner such that said compositions will be delivered to a mammal in a therapeutically effective amount, as part of a prophylactic, or therapeutic treatment to facilitate relaxation of organs build with smooth muscle cells and as such to relax the blood vessels and over the high blood pressure, relax the respiratory pathways important in asthma, relax uterus important in PMS, relax uterine track or gallbladder important in kidney or gallbladder stone all with or without prescribed pharmaceutical drug.

In certain embodiments, the dosage of the micronutrient compositions, which may be referred to as therapeutic composition provided herein, may be determined by reference to the plasma concentrations of the therapeutic composition or other encapsulated materials. For example, the blood pressure or lung function may be tested for determining the effect of micronutrient treatment in a mammal.

The therapeutic micronutrient composition provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject micronutrient composition of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject micronutrient composition that may be combined with a carrier material to produce a single dose may vary depending upon the subject being treated and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the micronutrient composition include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

INDUSTRIAL USE

Thus, in this study we prove that micronutrient composition plays a decisive role in regulating the high blood pressure in individuals. With optimum combination of natural ingredients and micronutrients the blood pressure is controlled at a significant level.

What is claimed is:

1. A high blood pressure reducing micronutrient composition, comprising:
a vitamin C in calcium ascorbate or magnesium ascorbate form in the range of 0.01 mg-5000 mg, vitamin B1 in the range of 0.1 mg-50 mg, vitamin B2 in the range of 0.1 mg-50 mg, vitamin B3 in the range of 1 mg-3000 mg, vitamin B6 in the range of 0.1 mg-50 mg, vitamin B12 in the range of 10 μg-300 μg, vitamin D in the range of 10 μg-400 μg, vitamin B9 (folate) in the range of 10 μg-5000 μg, magnesium in the range of 1 mg-5000 mg, celery extract in the range of 10 mg-2000 mg, grape seed extract in the range of 10 mg-1000 mg, clove extract in the range of 10 mg-1000 mg, green tea extract in the range of 10 mg-1000 mg and L-arginine in the range of 10 mg-10000 mg.

2. The micronutrient composition of claim 1, consisting of the vitamin C as calcium ascorbate in the range of 0.01 mg-5000 mg, vitamin B1 in the range of 0.1 mg-50 mg, vitamin B2 in the range of 0.1 mg-50 mg, vitamin B3 in the range of 1 mg-3000 mg, vitamin B6 in the range of 0.1 mg-50 mg, vitamin B12 in the range of 10 μg-300 μg, vitamin D in the range of 10 μg-400 μg, vitamin B9 (folate) in the range of 10 μg-5000 μg, magnesium in the range of 1 mg-5000 mg, celery extract in the range of 10 mg-2000 mg, grape seed extract in the range of 10 mg-1000 mg, clove extract in the range of 10 mg-1000 mg, green tea extract in the range of 10 mg-1000 mg and L-arginine in the range of 10 mg-10000 mg.

3. The micronutrient composition of claim 1, consisting of the vitamin C as magnesium ascorbate in the range of 0.01 mg-5000 mg, vitamin B1 in the range of 0.1 mg-50 mg, vitamin B2 in the range of 0.1 mg-50 mg, vitamin B3 in the range of 1 mg-3000 mg, vitamin B6 in the range of 0.1 mg-50 mg, vitamin B12 in the range of 10 μg-300 μg, vitamin D in the range of 10 μg-400 μg, vitamin B9 (folate) in the range of 10 μg-5000 μg, magnesium in the range of 1 mg-5000 mg, celery extract in the range of 10 mg-2000 mg, grape seed extract in the range of 10 mg-1000 mg, clove extract in the range of 10 mg-1000 mg, green tea extract in the range of 10 mg-1000 mg and L-arginine in the range of 10 mg-10000 mg.

4. The micronutrient composition of claim 1, further comprising a prescribed pharmaceutical drug to be used with the said micronutrient composition.

5. The micronutrient composition of claim 4, wherein the prescribed pharmaceutical drug is an angiotensin-converting enzyme inhibitor.

6. The micronutrient composition of claim 5, wherein the angiotensin-converting enzyme inhibitor is Lisinopril.

7. micronutrient composition to reduce high blood pressure. comprising;
a vitamin C in calcium ascorbate or magnesium ascorbate form in the range of 0.01 mg-5000 mg, vitamin B1 in the range of 0.1 mg-50 mg, vitamin B2 in the range of 0.1 mg-50 mg, vitamin B3 in the range of 1 mg-3000 mg, vitamin B6 in the range of 0.1 mg-50 mg, vitamin B12 in the range of 10 μg-300 μg, vitamin D in the range of 10 μg-400 μg, vitamin B9 (folate) in the range of 10 μg-5000 μg, magnesium in the range of 1 mg-5000 mg, celery extract in the range of 10 mg-2000 mg, grape seed extract in the range of 10 mg-1000 mg, clove extract in the range of 10 mg-1000 mg, green tea extract in the range of 10 mg-1000 mg and L-arginine in the range of 10 mg-10000 mg.

* * * * *